(12) United States Patent
Davenport et al.

(10) Patent No.: US 7,776,366 B2
(45) Date of Patent: Aug. 17, 2010

(54) METHOD AND NUTRACEUTICAL COMPOSITION FOR MAMMALS

(75) Inventors: David F. Davenport, Knoxville, TN (US); J. Eric Martin, Louisville, TN (US)

(73) Assignee: MD's Choice, Inc., Louisville, TN (US)

(*) Notice: Subject to any disclaimer, the term of this patent is extended or adjusted under 35 U.S.C. 154(b) by 2 days.

(21) Appl. No.: 11/837,199

(22) Filed: Aug. 10, 2007

(65) Prior Publication Data

US 2008/0003302 A1    Jan. 3, 2008

Related U.S. Application Data

(62) Division of application No. 10/692,064, filed on Oct. 23, 2003, now abandoned.

(60) Provisional application No. 60/420,743, filed on Oct. 23, 2002.

(51) Int. Cl.
*A01N 65/00*   (2009.01)
*A01N 43/04*   (2009.01)
*A61K 47/00*   (2006.01)
*A61P 15/08*   (2006.01)

(52) U.S. Cl. .......................... 424/725; 424/439; 514/62
(58) Field of Classification Search ................. None
See application file for complete search history.

(56) References Cited

U.S. PATENT DOCUMENTS

| | | | |
|---|---|---|---|
| 3,683,076 A | 8/1972 | Rovati | 424/180 |
| 4,774,089 A * | 9/1988 | Ashmead | |
| 5,364,845 A | 11/1994 | Henderson | 514/54 |
| 5,902,801 A | 5/1999 | Schleck et al. | 514/62 |
| 5,906,979 A | 5/1999 | Allan | 514/25 |
| 6,117,851 A | 9/2000 | Sherman et al. | 514/62 |
| 6,183,769 B1 | 2/2001 | Campbell et al. | 424/438 |
| 6,468,525 B1 * | 10/2002 | Watson et al. | |
| 6,558,911 B1 | 5/2003 | Sutovsky | 435/7.2 |
| 6,645,536 B2 | 11/2003 | D'Abramo | 426/72 |
| 6,838,451 B1 | 1/2005 | Menard et al. | 514/62 |
| 6,962,718 B2 * | 11/2005 | Ramaekers | |
| 7,015,207 B2 * | 3/2006 | Xu et al. | |
| 2002/0037314 A1 | 3/2002 | Meisner | 424/449 |
| 2002/0142052 A1 * | 10/2002 | Trant | |

FOREIGN PATENT DOCUMENTS

| | | | |
|---|---|---|---|
| JP | 76022078 B | * | 7/1976 |
| JP | 09047232 A | * | 2/1997 |
| WO | WO 01/01992 A1 | | 1/2001 |
| WO | WO 0101992 A1 | * | 1/2001 |

OTHER PUBLICATIONS

Kula, K et al. Molecular and Cellular Endocrinology vol. 178, Issues 1-2, Jun. 10, 2001, pp. 89-97. Estradiol enhances the stimulatory effect of FSH on testicular maturation and contributes to precocious initiation of spermatogenesis.*
http://www.merckvetmanual.com/mvm/index.jsp?cfile=htm/bc/90722.htm. The Merck Beterinary Manual. "Laminitis". Downloaded Oct. 11, 2009.*
Abe, T. et al., Journal of the Japanese Obstetrical & Gynecological Society, 1965, 12(4):235-8. Induction of ovulation by a new ovulation-inducing agent, copper N-succinyl glucosamate.

* cited by examiner

*Primary Examiner*—Michele Flood
(74) *Attorney, Agent, or Firm*—St. Onge Steward Johnston & Reens LLC

(57) ABSTRACT

A method is provided improving fertility in a mammal using glucosamine based composition. The composition is effective to improve fertility in mammals, including humans and stallions.

17 Claims, 4 Drawing Sheets

METHOD AND NUTRACEUTICAL COMPOSITION FOR MAMMALS

This applications is a divisional of U.S. patent application Ser. No. 10/692,064, filed Oct. 23, 2003, which claims the benefit under 35 U.S.C. §119(e) of the U.S. Provisional Patent Application Ser. No. 60/420,743 filed Oct. 23, 2002. All prior applications are herein incorporated by reference in their entirety.

FIELD OF THE INVENTION

The present invention relates to therapeutic compositions and methods for promoting fertility in mammals in need thereof. Furthermore, the invention relates to glucosamine based nutraceutical compositions capable of promoting fertility in a mammal.

BACKGROUND OF THE INVENTION

Sperm and egg generating processes in mammals are constantly subjected to stresses from physical, chemical, and biological sources that can result in problems whereby a male or female may become infertile or sub-fertile due to poor or insufficient semen or egg quality. These problems may be compounded in the cases of under or mal nourished mammals.

The treatment of sperm or egg afflictions can be quite problematic, especially in the case of humans and animals such as horses, where treatment is often directed at controlling the symptoms of the afflictions and not their causes, regardless of the stage of infertility, or sub-fertility. Improving sperm and egg quality may be significantly hampered, in the case where the mammal is under nourished or mal nourished and lacks the requisite building blocks to promote spermatogenesis or oogenesis. In these cases, medical or veterinarian assistance alone may not improve the quality and quantity of sperm.

Sperm are produced by the well known process of spermatogenesis where spermatogonia develop from primordial germ cells that migrate into the testis early in embryogenesis. In sexually mature male mammals, the spermatogonia divide to continually renew themselves, where some sperm further divide by meiosis to become primary spermatocytes, which in turn continue through meiotic division I to become secondary spermatocytes. After they complete meiotic division II, the secondary spermatocytes produce haploid spermatids that differentiate into mature sperm. Mature sperm comprise various components including a head and a tail. All of the steps in the process require the continuous input of cellular building blocks in order to adequately and correctly produce viable mature sperm.

Eggs are produced by a well known process called oogenesis. The process results in the formation of a large cell having a variety of resources for the construction of the embryo. Accordingly, oogenesis requires adequate nutrition to provide the cellular building blocks to create the equipped cells.

The basic cellular building blocks include, among other things, amino acids, carbohydrates, proteins, fats and saccharides. The present invention provides compositions having effective fertility promoting nutrients to enhance gametogenesis and the maintenance of sperm and egg cells, which ultimately promote fertility. Nutrients are required to play a role in the development and function of sperm and egg. Detailed knowledge of the role played by various nutrients or the level required for optimal development and function of sperm and egg are not well understood. Therefore, correcting key nutrient deficiency through supplementation has been problematic. The present invention overcomes these difficulties by providing compositions, mixtures, and dosage forms containing the key nutrients needed to improve fertility in mammals.

For many mammalian breeders, such as horse breeders, infertility is an aggravating problem forcing breeders to seek medical and veterinarian assistance. Such assistance may be costly and untimely with respect to the mating season. Accordingly, lower costing supplementation may alleviate the problems of infertility prior to seeking assistance.

Conventional treatments for various mammalian infertility conditions include the administration of human chorionic gonadotrophins (hCG), human menopausal gonadotrophin (hMG) (consisting of equal amounts of follicle stimulating hormone, FSH, and luteinizing hormone LH), or luteinizing hormone releasing hormone (LHRH), also known as gonadotrophin releasing hormones (GnRH). Treatment with these hormones however, is generally expensive, and does not always yield satisfactory results for certain males, such as those exhibiting idiopathic oligospermia.

An alternative medicinal treatment to the drugs described above are low cost 'natural' medicines such as various herbs which are typically ingested over large periods of time to form part of one's diet. Two examples of naturally occurring herbs thought to increase the human bodies' production of male hormones include ginseng and sarsaparilla. The roots of these herbs are thought to have the medicinal properties. However, it is inconclusive whether ingestion of these herbs does indeed promote spermatogenesis.

Patents of interest include U.S. Pat. No. 5,364,845 (herein incorporated by reference) which relates to a method and composition for the protection, treatment and repair of connective tissue in mammals. The composition includes glucosamine and chondroitin sulfate. The composition further includes manganese ascorbate which catalyzes the production of collagen and proteoglycans from the glucosamine and the chondroitin sulfate.

Furthermore U.S. Pat. No. 6,558,911 (herein incorporated by reference) relates to male infertility, and in particular to assays for predicting fertility in animals including human and bovines. In some embodiments, semen samples are evaluated by measuring the amount of ubiquitin in the sample, and in particular by measuring the extent of ubiquitination spermatozoa. Increased levels of ubiquitination in a sample are correlated with lower fertility.

Due to stress on sperm and egg cells from the continuously replicating nature of spermatogenesis, and the storage of egg cells, proper nourishment is essential to facilitate fertility and promote adequate amounts of viable gametes. Accordingly what is needed is a composition which alleviates, overcomes, or cures the problem of infertility and sub-fertility by ensuring that gamete generating tissues are nourished and have access to the cellular building blocks necessary for spermatogenesis, oogenesis and gamete maintenance. The compositions and methods of the present invention are applicable to males wherein the conception rate may be affected by physical, chemical, or biological stressors to the sperm or developing sperm in the target organ. Moreover, the compositions and methods of the present invention are applicable to females wherein the egg integrity may be affected by physical, chemical, or biological stressors to the egg or developing egg in the target organ.

The present invention relates generally to nutraceutical compositions and specifically to those compositions making use of glucosamine in promoting fertility. In particular, the compositions may be provided in dosage forms for treating infertile or sub-fertile mammals. The present invention provides improved compositions that require little technical expertise to use, are rapid, and may be used either as a nutritional supplement, or as a medicinal treatment of infertile or sub-fertile mammals.

SUMMARY OF THE INVENTION

It is an object of the invention to provide a composition for increasing fertility in mammals.

It is the object of the present invention to increase dietary intake of vitamins and minerals associated with the gametogenesis in mammals.

It is a further objective of the present invention to provide a method for improving conception rates in a mammal.

It is an object of the invention to provide a method and composition for increasing fertility in stallions.

It is a further object of the present invention to improve conception rates in mammals.

It is a further object of the present invention to provide digestive tract support in mammals.

It is a further object of the present invention to provide a nutraceutical composition having a long shelf life.

It is a further object of the present invention to provide a nutraceutical composition that is multifunctional.

These and other objectives of the present invention are obtained by providing a nutraceutical composition comprising a glucosamine component present in an effective proportion such that, when administered to a mammal in an effective amount, the nutraceutical composition is effective to improve fertility. The glucosamine component is selected from the group consisting of glucosamine sulphate, glucosamine sulfate 2KCL, glucosamine sulfate NaCl, glucosamine hydrochloride, N-acetylglucosamine, Poly-Nag. glucosamine, and combinations of these chemicals. The composition may further be provided in a solid dosage form, and/or a dry powder dosage form and/or a liquid dosage form, and combinations of these dosage forms. Mammals include human, bovine, equine, caprine, ovine, and porcine subjects.

The objectives of the present invention are further obtained by providing a nutraceutical composition comprising the following constituents: an oil cake component; a glucosamine component; an acid component; a mineral component; a vitamin component; and a functional food component, wherein each constituent is present in an effective proportion such that, when administered to a mammal in an effective amount, the nutraceutical composition is effective to improve fertility. The oil cake component is selected from the group consisting of soybean flower, linseed oil cake, cottonseed oil cake, peanut oil cake, safflower oil cake, coconut oil cake, palm oil cake, sesame oil cake, sunflower oil cake, rapeseed oil cake, kapok oil cake, mustard seed oil cake, and combinations of these. The glucosamine component is a chemical selected from the group consisting of glucosamine sulphate, glucosamine sulfate 2KCL, glucosamine sulfate NaCl, glucosamine hydrochloride, N-acetylglucosamine, Poly-Nag. glucosamine, and combinations of these. The composition further contains an acid component such as ascorbic acid and/or at least one derivative of ascorbic acid, lipoic acid, or dihydrolipoic acid, wherein the derivative of ascorbic acid is selected from the group consisting of magnesium ascorbyl phosphate, sodium ascorbyl phosphate, sodium ascorbate, ascorbyl glucoside, and combinations thereof. The composition may further comprise a mineral component further comprising at least one mineral selected from the group consisting of zinc, boron, chromium, manganese, and combinations of these. The composition comprises a mineral acid component characterized as an amino acid chelate. The composition may additionally include a vitamin component wherein said vitamin component further comprises at least one vitamin selected from the group consisting of biotin, thiamine HCL, folic acid, and combinations thereof. The composition may further contain a functional food component that further comprises an ingredient selected from the group consisting of prebiotic, probiotic, synbiotic and combinations of these. This embodiment may further comprise components of the nutraceutical composition present in the following approximate effective proportions: between about 50 and about 200 pbw oil cake, between about 400 to 750 pbw glucosamine component, between about 50 and about 150 pbw acid component, between about 0.0001 and about 1 pbw mineral component, between about 0.0001 about 1 pbw vitamin component, between about 0.0001 and about 1 pbw of functional food component. Such compositions may be administered to a patient in need thereof in an effective amount in a powder dosage form. Suitable subjects include a male or female mammal such as a horse.

The objectives of the present invention are further obtained by providing a nutraceutical composition comprising the following constituents: soybean flour, glucosamine sulphate 2KCL, sodium ascorbate, manganese, chromium, boron, zinc, biotin, thiamine HCL, folic acid, and a functional food component, wherein each constituent is present in an effective proportion such that, when administered to a mammal in an effective amount, the nutraceutical composition is effective to improve fertility. The mammal may be, among other things, a male or female human or horse.

The objectives of the present invention are further obtained by providing a nutraceutical composition comprising the following constituents: a glucosamine component, and a nutrient component, wherein each constituent is present in an effective proportion such that, when administered to a mammal in an effective amount, the nutraceutical composition is effective to improve fertility. Such composition may use a nutrient component that further comprises at least one ingredient selected from the group consisting of oil cake component, acid component, mineral component, vitamin component, functional food component, and combinations of these. Such composition may be in a dosage form selected from the group consisting of solid dosage form, dry powder dosage form, liquid dosage form, and combinations thereof. Such composition may be useful for a mammal such as human, bovine, equine, caprine, ovine, and porcine.

The objectives of the present invention are further obtained by providing a method for improving fertility in a mammal comprising the step of administering to the mammal gametogenesis promoting effective amount of a nutraceutical composition comprising the following constituents: an oil cake component, a glucosamine component, an acid component, a mineral component, a vitamin component, and a functional food component, wherein each of the constituents is present in the composition in an effective proportion. Such method further includes providing a nutraceutical composition in an oral liquid dosage form, or a dry powder form. The mammal may be, among other things, a male or female human or horse. The mammal may be a stallion. Such a method having an effective proportion comprising: between about 50 and about 200 pbw oil cake component, between about 400 to 750 pbw glucosamine component, between about 50 and about 150 pbw acid component, between about 0.0001 and about 1 pbw mineral component, between about 0.0001 and about 1 pbw vitamin component, and between about 0.0001 and about 1 pbw of functional food component. Such a method may include a glucosamine component which is a chemical selected from the group consisting of glucosamine sulphate, glucosamine sulfate 2KCL, glucosamine sulfate NaCL, glucosamine hydrochloride, N-acetylglucosamine, Poly-Nag. glucosamine, and combinations of these chemicals. Such a method may optionally include an acid component wherein the acid component is ascorbic acid and at least one derivative thereof, lipoic acid, or dihydrolipoic acid, wherein the derivative is selected from the group consisting of magnesium ascorbyl phosphate, sodium ascorbyl phosphate, sodium ascorbate, ascorbyl glucoside, and combinations thereof. Such a method may optionally include a mineral component wherein said mineral component further comprises at least one mineral selected from the group consisting of zinc, boron, chromium, manganese, and combinations thereof. Such a method may further include the mineral acid component characterized as an amino acid chelate. The method may further provide a vitamin component further comprising at least one vitamin selected from the group consisting of biotin, thiamine HCL, folic acid, and combinations thereof. The method optionally may include a functional food component further comprising at least one ingredient selected from the group consisting of prebiotic, probiotic, synbiotic, and combinations thereof. The method may use an oil cake which is characterized as a vegetable oil cake. Further, the method may further include an oil cake component selected from the group consisting of soybean flower, linseed oil cake, cottonseed oil cake, peanut oil cake, safflower oil cake, coconut oil cake, palm oil cake, sesame oil cake, sunflower oil cake, rapeseed oil cake, kapok oil cake, mustard seed oil cake, and combinations thereof.

The objectives of the present invention are further obtained by providing a therapeutic composition for the treatment, repair, or increased production of gametocytes in mammals, comprising: therapeutic quantities of glucosamine and salts thereof, in combination with a nutrient component, for effectively promoting fertility in mammals in need thereof. Such a composition may optionally include glucosamine selected from the group consisting of glucosamine hydrochloride, glucosamine sulphate, glucosamine sulphate 2KCL, glucosamine sulphate NaCL, and combinations thereof. Such a composition may further optionally be, or be administered as a dose, wherein the dose of glucosamine ranges of from about 1 g to about 50 g per day. Such a composition may further optionally be comprise a therapeutic quantity of glucosamine for horses or large mammals which is approximately 20 g per day. The gametocytes may be a mammalian sperm or an egg.

The objectives of the present invention may further be obtained by providing a method for improving fertility in a mammal comprising the step of administering to the mammal gametogenesis promoting effective amount of a nutraceutical composition comprising the following constituents: a glucosamine component, a nutrient component, wherein each of the constituents is present in the composition in an effective proportion. Such a method may optionally be administered as an oral liquid dosage form, or a dry powder form. Such a method is suitable for a mammal which may be a human, horse, dog, cow, pig, sheep, or lab animal.

DEFINITION OF TERMS

The following definitions apply throughout the present specification:

The term "oil cake" refers to the refuse of flax seed, cotton seed, or other vegetable substance from which oil has been expressed, compacted into a solid mass, and used as food, for manure, or for other purposes. The term further refers to suitable vegetable substances such as soybean flower, linseed oil cake, cottonseed oil cake, peanut oil cake, safflower oil cake, coconut oil cake, palm oil cake, sesame oil cake, sunflower oil cake, rapeseed oil cake, kapok oil cake, mustard seed oil cake, and the like.

The term "nutrient" refers to any substance that furnishes nourishment to an animal. The term further refers to substances such as protein, fat, carbohydrate, simple sugar, functional food, vitamin, mineral, prebiotic, probiotic, synbiotic, acid, base, or salt that provides nourishment to an animal. The term further refers to complexes of protein, fat, carbohydrate, simple sugar, vitamin, mineral, prebiotic, probiotic, synbiotic, acid, base, or salt that provides nourishment to an animal.

The term "probiotic" refers to substance or organism which contributes to intestinal microbial balance in an animal. The term further refers to living organisms in foods and feeds or dietary supplements which contribute to intestinal microbial balance in an animal.

The term "prebiotic" refers to a substance or ingredient that when provided to the digestive tract selectively supports the growth of beneficial bacterial species over pathogenic ones. The term further refers to substances that do not directly colonize the digestive tract. The term prebiotic further refers to, but is by no means limited to yeast, yeast cultures, fungal cultures, and preferably, certain fibers (FOS-fructooligosaccharides).

The term "synbiotic" refers to substances or ingredients that contain both prebiotic and probiotic ingredients. The term further refers to a prebiotic and probiotic blend for gastrointestinal support.

The term "functional food" refers to a food which contains one or a combination of components which affects functions in the body so as to have positive cellular or physiological effects. The term further refers to prebiotic(s), probiotic(s), and/or synbiotic(s).

The term "parts by weight", abbreviated "pbw", is given its usual and customary meaning wherein a part can be expressed with reference to any convenient unit of measure, for example ounce or gram. When used with respect to a component or constituent, pbw is with reference to the total nutraceutical composition. For components or constituents that can include water of crystallization (hydration), pbw are based on the component or constituent in the non-hydrated form. The term "pbw" refers to a mix ratio as parts by weight. The term refers generally to mixing by weight.

The term "fertility" refers to the quality or state of being fertile. The term further refers to a male or female mammal being capable of breeding or reproducing.

The term "mammal" refers to any of a class (Mammalia) of warm-blooded higher vertebrates (as placentals, marsupials, or monotremes) that nourish their young with milk secreted by mammary glands, have the skin usually more or less covered with hair, and include humans. The term further refers to domestic animals, such as feline or canine subjects, farm animals, such as but not limited to bovine, equine, caprine, ovine, and porcine subjects, wild animals (whether in the wild or in a zoological garden), research animals, such as mice, rats, rabbits, goats, sheep, pigs, dogs, cats, etc., avian species, such as chickens, turkeys, songbirds, etc., i.e., for human or veterinary medical use.

DETAILED DESCRIPTION OF THE INVENTION

Figure 1:
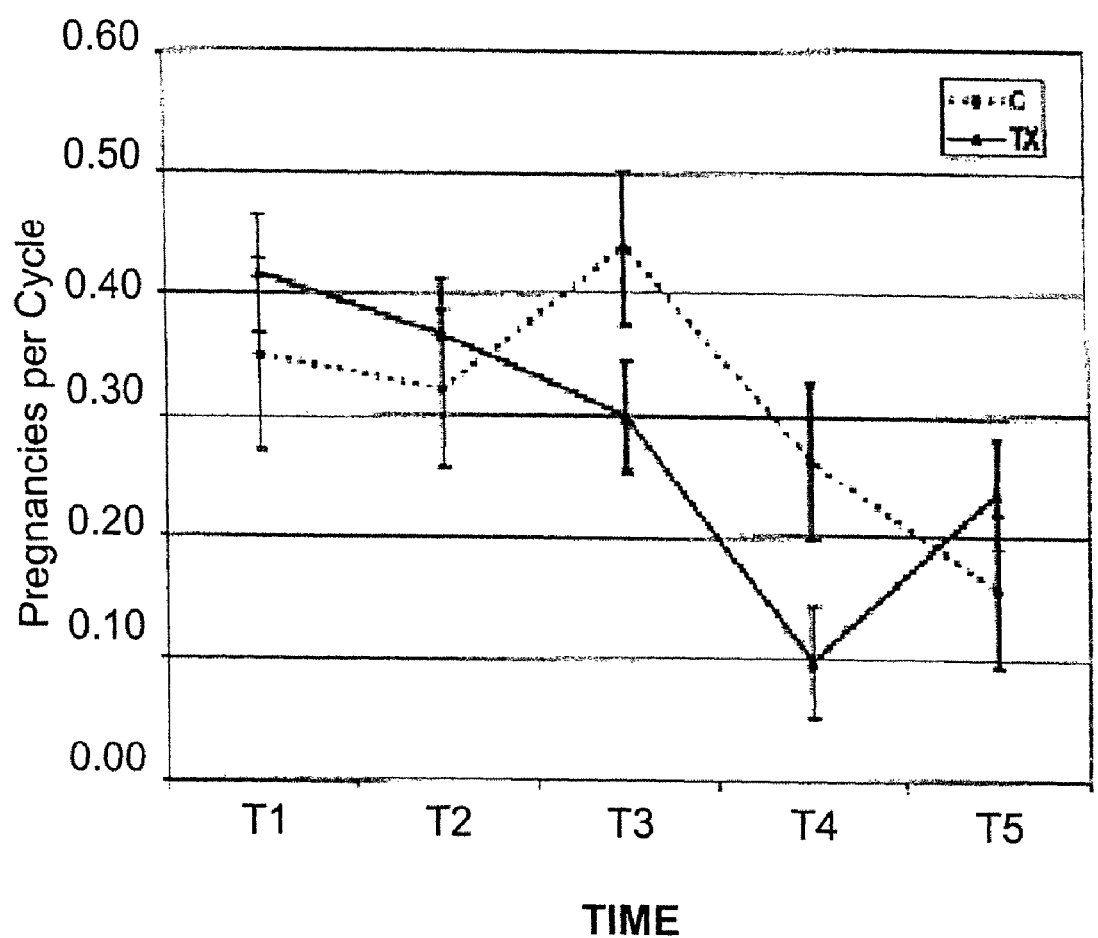
FIG. 1 is a graph of pregnancies per cycle over time.

The composition of the present invention includes an oil cake component, a glucosamine component, an acid component, a mineral component, a vitamin component, and preferably a symbiotic component. According to the principles of the present invention, a composition of oil cake, an acid component, a mineral component, a vitamin component, and preferably a symbiotic component, and in combination with a glucosamine component, all of which are introduced from or produced outside the mammal, are administered to a mammal in need thereof. The composition is provided so as to be available for use by the mammal's spermatogenesis processes to manufacture sperm and promote sperm maintenance, and thus is useful in the prophylaxis or treatment, for example, of conditions or diseases in which enhanced sperm quality or sperm proliferation are desirable, among other desirable activities. The composition is further provided so as to be available for use by the mammal's oogenesis processes to manufacture egg and promote egg maintenance, and thus is useful in the prophylaxis or treatment, for example, of conditions or diseases in which enhanced egg quality or egg proliferation are desirable, among other desirable activities, such as enhancing attachment sites on the egg to improve conception.

Glucosamine is rapidly available to mammals after oral administration, and is a very small building block type nutrient that is found ubiquitously in mammalian tissue. Glucosamine is actively concentrated in some tissues such as connective tissue and all mucosal linings. Many important reproductive cells and structures contain large concentrations of glucosamine. Most of the glucosamine containing structures mentioned contain the acetylated form of glucosamine linked together by sulphur bonds. However, this form has been shown to be highly utilized in the digestive tract, with only small amounts being absorbed by the body. Absorption of the acetylated form occurs via passive diffusion. Glucosamine sulphate is, however, absorbed actively from the digestive tract using a glucose transporter. This active absorption has been shown to be over 90% efficient within 30 minutes in at least 3 species. The acetylation of glucosamine sulphate as well as its conversion to galactosamine is readily performed in most tissues. Supplying large amounts of a purified nutrient alone may not positively affect the desired systems and can have negative effects. Furthermore, both chondroitin sulfate and injectable PSGAG's may cause decreased stallion reproductive performance due to the large size of these molecules.

Several male and female reproductive structures utilize glucosamine, including but not limited to, lining of the uterus and cervix, Zona pellucida of the egg, attachment site of egg to sperm, implantation site of the embryo into the uterus, cell to cell adhesion in early development of the cumulus mass, testies, sperm membrane, seminal fluid, and the acrosomal end of the sperm. Moreover, glucosamine plays a role in a variety of chemical reactions, including a role in Acrosomal reaction. Administered glucosamine localizes to male reproductive tissues, where it becomes available for spermatogenesis. Administered glucosamine localizes to female reproductive tissues, where it becomes available for oogenesis, conception and embryonic development. Moreover, it has been surprising found that supplementation with glucosamine enhances the seminal fluids and uterus to create a more favorable environment for conception, implantation, and gestation leading to improved fertility.

The glucosamine component is the base of the composition and may include glucosamine sulphate, glucosamine sulfate 2KCL, glucosamine sulphate NaCL, glucosamine hydrochloride, N-acetylglucosamine and Poly-Nag. glucosamine. It has been found that glucosamine sulfate 2KCL is preferred in certain embodiments. The glucosamine component is, preferably, in a salt form so as to facilitate its delivery and uptake by the mammal. The salt forms include glucosamine hydrochloride, glucosamine sulfate, glucosamine sulphate NaCL, and glucosamine sulphate 2KCL.

Various amounts of glucosamine may be added to the composition of the present invention. The composition may contain between about 400 to 750 pbw glucosamine component, optionally between about 500 to about 700 pbw glucosamine component, preferably about 600 pbw glucosamine component. For example 1 Kg of composition preferably comprises about 600 g of glucosamine component such as glucosamine sulphate 2 KCL. The glucosamine component may be supplied from any distributor of glucosamine components. Moreover, in some embodiments, the glucosamine component may comprise 100% of the composition.

Another component of the composition is oil cake. Examples of the suitable oil cakes include vegetable oil cakes such as soybean oil cake, linseed oil cake, cottonseed oil cake, peanut oil cake, safflower oil cake, coconut oil cake, palm oil cake, sesame oil cake, sunflower oil cake, rapeseed oil cake, kapok oil cake and mustard seed oil cake. Soybean flower is the preferred oil cake in certain embodiments. The oil cake component is a source of protein for mammals such as a horses, cattle or sheep and provides a major portion of the protein for spermatogenesis. Protein is one of the main building blocks of the body, and is a major component of muscles, the nervous system and connective tissue. Adequate dietary protein is essential for maintenance, growth, lactation and reproduction. Oil cake provides the additional benefit of increasing the intake and digestibility of roughages in a mammals diet, such as a horse, making cellular building blocks available for gametogenesis. The oil cake component provides an optimal source of protein to promote gametogenesis.

Various amounts of oil cake may be added to the composition of the present invention. The composition may contain between about 50 to 200 pbw oil cake component, optionally between about 75 to about 150 pbw oil cake component, preferably about 145 pbw oil cake component. For example 1 Kg of composition preferably comprises about 145 g of oil cake component such as soybean flower. The oil cake component may be supplied from any distributor of oil cake.

Another component of the composition is acid. Suitable acid component of the composition include ascorbic acid, derivatives of ascorbic acid, lipoic acid, and dihydrolipoic acid. The derivatives of ascorbic acid include magnesium ascorbyl phosphate, sodium ascorbyl phosphate, sodium ascorbate, and ascorbyl glucosides. Preferably the acid component is sodium ascorbate in certain embodiments.

Various amounts of acid component may be added to the composition of the present invention. The composition may contain between about 50 to 150 pbw acid component, optionally between about 75 to about 125 pbw acid component, preferably about 100 pbw acid component. For example 1 Kg of composition preferably comprises about 100 g of acid component such as sodium ascorbate. The acid component may be supplied from any distributor of acid components.

Another component of the present invention is a mineral component. Minerals act as cofactors for enzymes for almost every reaction in the body and mineral deficiency affects immune system function, bone density, protein, fat, and carbohydrate metabolism. It has been found that providing a mineral component in the composition promotes fertility for mammals in need thereof. The mineral component is preferably provided in an amino acid chelate form due to the increased bioavailability of these forms. Less preferably, other organic mineral complexes such as sulfates, citrates, gluconates, and lactates may be utilized and have been found to have higher biological value than the least preferred inorganic mineral complexes (oxides, carbonates). Several minerals are associated with increased reproductive performance in both males and females. The form that minerals are supplied in is critical. All of the minerals listed below have reported toxic effects on reproduction, when exposure is to the inorganic forms, and beneficial effects when exposure is from organic forms.

Boron is an ultra-trace mineral and is a good example of a nutrient that is beneficial to the spermatogenic cycle, embryonic, and fetal development when provided in an organic form. However, if the exposure is to an inorganic form, testicular damage and mutagenic effects are common. Boron is involved in the production of many sex hormones.

Chromium is also an ultra-trace mineral whose deficiency can cause a decrease in sperm count, but exposure to inorganic forms can cause severe testicular damage, improper testicular development, or neoplasia. Many positive effects on female reproductive efficiencies and lactation improvements have been found.

Manganese is a trace mineral that is essential for growth, reproduction, prevention of skeletal abnormalities, and congenital ataxia. Manganese usually localizes in the cell's mitochondria. Manganese is the metal cofactor (preferred) for a number of glycosyltransferases which provides the link between biochemical function and deficiency symptoms. Manganese also plays an important role in carbohydrate, lipid, and brain metabolism. Research has shown that manganese plays a large part in attachment and conception. Exposure to inorganic manganese causes extremely reduced male fertility.

Zinc is a trace mineral whose deficiency has negative effects on testosterone levels and sperm development. Normal growth and lactation are both dependant on the presence of adequate amounts of zinc. Exposure to inorganic zinc causes harm to male and female reproductive tissues.

Suitable minerals for the composition include zinc, boron, chromium and manganese, however any mineral associated with increase reproductive performance in males can be used. Various amounts of organic manganese, chromium, boron and zinc may be used. The composition may contain between about 0.001 to 1.0 pbw mineral component, optionally between about 0.004 to about 0.0095 pbw mineral component, preferably about 0.009 pbw mineral component. For example 1 Kg of composition preferably comprises about 9 g of mineral component.

The mineral component preferably is a mixture of minerals having various amounts of each mineral. 1 Kg of composition may contain between about 3 g to about 4.5 g of manganese, preferably 4 g; between about 0.01 g to about 0.2 g of chromium, preferably 0.15 g; about 0.5 to about 0.1 g of boron, preferably 0.75 g; and about 2 to about 4 g of zinc, preferably 3 g.

Most preferably, the mineral component is a mixture of various fertility promoting minerals in amino acid chelate (AAC) form. The AAC form comprises a complex between the amino acid and the mineral. Preferably the AAC mineral component is a mixture of zinc AAC, boron AAC, chromium AAC and manganese AAC having various amounts of each mineral. 1 Kg of composition may contain between about 15 g to about 30 g of manganese AAC (16%), preferably 25 g; between about 3 g to about 9 g of chromium AAC (2.5%), preferably 6 g; about 0.5 to about 0.1 g of boron AAC (2.5%), preferably 30 g; about 10 to about 20 g of zinc AAC (20%), preferably 15 g. Accordingly, the composition contains between about 0.025 to 0.100 pbw mineral component in complex form, optionally between about 0.50 to about 0.085 pbw mineral component in complex form, preferably about 0.076 pbw mineral component in complex form. For example 1 Kg of composition preferably comprises about 76 g of mineral component in AAC form. Preferably, the minerals are elemental amounts of albion chelates.

Another component of the present invention is a vitamin component. Vitamins are categorized into two distinct classes: water soluble and fat soluble. Water soluble vitamins are not stored in the body; they are excreted if not utilized soon after ingestion. Fat soluble vitamins (Vitamins A, D, E, and K) are stored and have more of a potential for toxicity. Horses on premium commercial feeds rarely develop a clinical deficiency of an individual mineral or vitamin because the feeds are appropriately fortified. General supplements should not be used to try to make a good ration out of poor quality feedstuffs. They can be used to support horses that are under more stressful conditions such as performance, reproductively active, diseased, or geriatric.

Folic acid is a water soluble vitamin that plays critical roles in the normal reproduction of cells. A deficiency of folate has been associated with defects in pre-implantation embryos and the neural, skeletal, digestive and urinary tracts of developing fetuses.

Biotin is a water soluble vitamin that has been heavily researched in many species with respect to its effect on female reproductive performance parameters and gamete development. The most well documented effects are on sow conception rates and return to estrus post parturition. Many effects of biotin on prenatal development have also been established.

Thiamine is a water soluble vitamin that is crucial to the viability and motility of sperm. Normal development in the uterus depends on the presence of thiamine.

Suitable vitamins for the composition include biotin, thiamin HCL, and folic acid; however any vitamin associated with increase reproductive performance in males can be used. Various amounts of each vitamin may be used. The composition may contain between about 0.001 to 1.0 pbw vitamin component, optionally between about 0.004 to about 0.0095 pbw vitamin component, preferably about 0.013 pbw vitamin component. For example 1 Kg of composition preferably comprises about 13 g of vitamin component.

The vitamin component preferably is a mixture of vitamins having various amounts of each vitamin. 1 Kg of composition may contain between about 0.2 g to about 1 g of biotin (1%), preferably 0.5 g; between about 5.0 g to about 15 g of thiamin HCL (87.4%), preferably 11 g; about 0.5 to about 1.5 g of folic acid, preferably 0.95 g.

Prebiotics are ingredients that when provided to the digestive tract selectively support the growth of beneficial bacterial species over pathogenic ones. Prebiotics do not directly colonize the digestive tract. Prebiotics include yeast, yeast cultures, fungal cultures, and preferably, certain fibers (FOS-fructooligosaccharides). Probiotics are the actual bacterial species that, when introduced to the digestive tract actually colonize and produce beneficial effects. Preferably probiotics of the composition include *Lactobacillus* and *Bifido*. Synbiotics are products that contain both prebiotic and probiotic ingredients. Ingredients of this type are important to include in a nutritional support program. As used herein, synbiotic refers to a prebiotic and probiotic blend for gastrointestinal support. The synbiotic of the present composition is preferably a prebiotic and probiotic blend of *Lactobacillus* and *Bifido*, and FOS-fructooligosaccharides. Although various amounts of these ingredients may be combined in a mixture, supplied blends are available from distributors of theses substances. Suitable blends for preferred embodiments of the present invention include probiotics from UAS Laboratories (product name is UAS Probiotic Blend), including the ingredients *Bifidobacterium longum* and *Lactobacillus acidophilus*, rice starch and fructooligosaccharides. The potency is over 10 billion Colony Forming Units per gram at the time of manufacture. This product may be blended with other constituents of the present invention.

Other nutrients may be used to support the digestive tract in mammals to promote fertility. For example, N-acetyl-D-glucosamine is a structural component of all mucosal surfaces. Supplementation with N-acetylglucosamine may help firm up the structural matrix of the intestinal tract. Though glucosamine appears to be highly absorbable, N-acetyl-glucosamine is directly incorporated into the intestinal mucosa and is not absorbed when provided orally. This improves the overall health of the intestinal tract under stress thereby contributing to its healing and increased absorption of other nutrients. Glutamine supplementation may further be incorporated to meet increased energy needs of the enterocytes in diseased or stressed states. 80% of the dietary intake of the amino acid glutamine is used by the enterocytes as energy in normally functioning digestive tracts. Increased intakes will support cell replication and function. Arginine has been found in human burn patients to promote the release of intestinal hormones and growth factors in the intestinal tract when given orally. It also increases blood flow to the digestive tract which promotes fertility by ensuring that nutrients have a greater chance of being absorbed.

A subject in whom administration of a nutraceutical composition of the invention in an effective therapeutic regiment for a disease or condition exemplified above, but not so limiting, is preferably a mammal. Thus, as can be readily appreciated by one of ordinary skill in the art, the methods and nutraceutical compositions of the present invention are particularly suited to administration to any animal, particularly a mammal, and including, but not limited to, humans, domestic animals, such as feline or canine subjects, farm animals, such as but not limited to bovine, equine, caprine, ovine, and porcine subjects, wild animals (whether in the wild or in a zoological garden), research animals, such as mice, rats, rabbits, goats, sheep, pigs, dogs, cats, etc., avian species, such as chickens, turkeys, songbirds, etc., i.e., for human or veterinary medical use.

The appropriate effective dosage of an agent of the invention may be readily determinable to the ordinary skilled worker with the understanding that the composition may be supplied to the average size stallion (up to 1300 pounds) at a rate of 20 g per day. The dosage may be supplied once a day, twice a day, or three times a day, preferably twice a day. For example, a 20 g dosage form would be divided into two 10 g forms and provided in the morning and evening. Supplementation should begin 60 days prior to the breeding season, to support all stages of the spermatogenic cycle. As supported in the examples, infra, a dosage approximately equal to the equivalent of 15 g/day to about 25 g/day, and more preferably, about 20 g/day is therapeutically effective in the fertility challenged stallions. The dosing schedule may vary, depending on the circulation half-life, and the formulation used.

The compositions are intended to be supplemented to male or female mammals. For example, in the equine group, supplementation may be provided to a stallion or a mare. It is noted however, that mares which become pregnant due to a deficiency being filled by compositions of the present invention may lose the pregnancy if supplementation is discontinued before foaling. Ending supplementation prior to full gestation in the female is not recommended. Accordingly, supplementation to stallions may be more cost effective.

The composition of the present invention preferably includes, in certain embodiments, glucosamine sulphate 2KCL (a quality chondroprotective), soybean flour, sodium ascorbate (product stabilizer and increases shelf life), biotin, boron amino acid chelate, manganese amino acid chelate, zinc amino acid chelate, synbiotics (Prebiotic & Probiotic Blend for GI support), Thiamine HCl, chromium amino acid chelate, and folic Acid.

The composition of the present invention preferably includes in certain embodiments the following constituents; a) a glucosamine component; and b) a nutrient component. In such embodiments each constituent is present in an effective proportion such that, when administered to a mammal in an effective amount, the nutraceutical composition is effective to improve fertility. In such embodiments that glucosamine component is between about 400 to about 700 pbw of the composition. In such embodiments, the nutrients may range between 1 and 600 pbw of the composition. Although not preferred a filler containing no nutrients may be included.

In other preferred embodiments the composition of the present invention preferably includes only a glucosamine component. In such embodiments the glucosamine component is present in an effective proportion such that, when administered to a mammal in an effective amount, the nutraceutical composition is effective to improve fertility. In such embodiments the glucosamine component is virtually all of the composition. For example such embodiments include glucosamine sulphate, glucosamine sulfate 2KCL, glucosamine sulphate NaCL, glucosamine hydrochloride, N-acetylglucosamine and Poly-Nag. glucosamine and mixtures thereof. It has been found that 100% glucosamine sulfate 2KCL is preferred in certain embodiments. The glucosamine component is, preferably, in a salt form so as to facilitate its delivery and uptake by the mammal. The salt forms include glucosamine hydrochloride, glucosamine sulfate, glucosamine sulphate NaCL, and glucosamine sulphate 2KCL.

Benefits of the present invention include:

Multi-functional promotion of reproduction, gastro-intestinal and connective tissues;

Enhanced fertility;

Improved conception rate;

Digestive tract support;

Support of joint and other connective tissues;

Ultra concentrated;

No palatability problems;

Long shelf life;

Veterinarian supported and formulated.

The various components are generally mixed by weight in a blender or mixing bowl, which may include utilizing an accurate scale (e.g. gram scale). However, mixing by volume may also be appropriate.

The composition may be administered to a variety of dosage forms known in the art including a capsule, tablet, or dry powder form. Capsules and tablets are manufactured according to known techniques where the mixture of components is either filled in a capsule, or compressed into a tablet. Preferably, the compositions are administered in a dry powder dosage form for ease of supplementation to feed.

Having discussed the composition of the present invention, it will be more clearly perceived and better understood from the following specific examples.

For large mammals such as horses, the composition I is administered as filled scoops.

Large Animal (Equine)
Level Scoopful (5 cc)
Composition I

| Component | Amount |
| --- | --- |
| Soybean Flower | 145 g |
| Glucosamine Sulphate 2KCL | 600 g |
| Sodium ascorbate | 100 g |
| Manganese | 4.0 g |
| Chromium | 0.15 g |
| Boron | 0.75 g |
| Zinc | 3.0 g |
| Biotin (1%) | 0.50 g |
| Thiamin HCL (87.4%) | 11.362 g |
| Folic Acid (95%) | 0.95 g |
| Probiotic blend | 15 g |

Preferrably, the following composition, composition II, is used for large mammal such as a horse.

Large Animal (Equine)
Level Scoopful (5 cc)
Composition II

| Component | Amount |
| --- | --- |
| Soybean Flower | 145 g |
| Glucosamine Sulphate 2KCL | 600 g |
| Sodium ascorbate | 100 g |
| Manganese AAC (16%) | 25 g complex |
| Chromium AAC (2.5%) | 6.0 g complex |
| Boron AAC (2.5%) | 30 g complex |
| Zinc AAC (20%) | 15 g complex |
| Biotin (1%) | 50 g complex |
| Thiamin HCL (87.4%) | 13 g complex |
| Folic Acid (95%) | 1.0 g complex |
| Probiotic blend | 15 g |

The following case study was conducted with mammals. The unexpected increased fertility of stallions demonstrates the effectiveness of the treatment.

Case #1

A study was conducted to evaluate the effect of a composition comprising glucosamine sulphate 2KCL, soybean flour, sodium ascorbate (product stabilizer and increase shelf life), biotin, boron amino acid chelate, manganese amino acid chelate, zinc amino acid chelate, synbiotics (prebiotic and probiotic blend for GI support), Thiamine HCl, Chromium Amino Acid Chelate, and folic acid on pregnancies per cycle and semen quality among commercial breeding stallions on a farm in middle Tennessee. Walking Horse stallions (n=12) were fed the nutritional supplement (treatment group) or a placebo (control group) as a top dressing on a commercial concentrate feed ration beginning in late April. Mares were bred using artificial insemination between mid-April and mid-August. Semen quality (ejaculate volume, sperm concentration, motility, morphology and viability) was evaluated during a 20-week period between early-April and mid-August. For purposes of comparison with data gathered in the treatment year, pregnancy data from the previous season was retrospectively evaluated for the control and treatment stallions. Pregnancy data was analyzed using a mixed model ANOVA procedure (PROC Mixed) with repeated measures, while semen quality data was analyzed using PROC GLM with repeated measures. In the year prior to treatment, mares were pregnant in 65/215 (30%) and 83/351 (24%) cycles following breeding to control and treatment stallions, respectively. During the treatment year, mares were pregnant in 53/179 (30%) and 86/223 (39%) cycles when bred to control and treatment stallions, respectively.

The proportion of pregnancies was not different between the pretreatment and treatment years for the control stallions, while the treatment stallions achieved a significantly higher proportion of pregnancies during treatment as compared with the previous season ($P<0.05$). However, the proportion of pregnancies did not differ between treatment and control stallions in the treatment year ($P>0.05$). Semen quality did not differ between treatment and control stallions. Results of this study provide evidence that the provided composition may improve pregnancies per cycle for stallions.

The composition was provided to a Tennessee Walking Horses at a commercial breeding farm in middle Tennessee. Stallions (n=12) standing at stud and the mares booked to them and managed on the farm during the 2000 (n=338) and 2001 (n=255) seasons were included in the study. Stallions were grouped by age and then randomized to a treatment or control group for the 2001 season. Fertility data from the 2000 breeding season was collected from farm records for comparison with reproductive performance in the 2001 season.

Farm personnel were blinded to the group assignment of each stallion. Stallions were fed the nutritional supplement (treatment group) or a placebo consisting of inert and inactive ingredients (control group). A total of 15 grams of treatment or placebo was divided between AM and PM feedings and fed as a top dressing on a concentrate feed ration starting on Apr. 23, 2001.

Breeding management was consistent among all horses in the study and representative of large commercial breeding facilities around the country. All mares were bred by artificial insemination. Semen was collected by artificial vagina from each stallion as required for breeding management of the mares. Ejaculate volume, concentration of sperm, and motility were assessed by farm personnel trained in semen analysis. Total sperm number in an ejaculate was calculated from the volume and sperm concentration data. Slides were prepared using an eosin-nigrosin morphology stain and sent to an outside laboratory for evaluation of sperm morphology and viability. Results were reported as a percentage of morphologically normal sperm and sperm excluding stain (viable).

The evaluation period for pregnancy outcome in each year was divided into 5 time periods. Time period 1 (T1) included data between February 1 and April 24. Time periods 2-5 (T2-T5) consisted of 4 week intervals from April 25 through the middle of August. The evaluation period for semen quality included 3 pre-treatment weeks (WK1-WK3) and 17 weeks (WK4-WK20) of treatment.

Pregnancy data was analyzed using a mixed model ANOVA procedure (PROC Mixed) with repeated measures.

The model consisted of a dependent variable, percent pregnant and independent class variables, treatment, year and time period (1-5). Stallion was included in the model as a random factor. Semen quality data was analyzed using PROC GLM with repeated measures.

All mares were bred by artificial insemination, therefore effects on conception rates were not due to changes in total sperm per ejaculate. Only mares bred on farm using fresh semen and whose 16-day pregnancy status confirmation was preformed on farm were used. These selection criteria resulted in a higher proportion of "problem mares" which explains the below industry average conception rates for both the control and treatment groups.

Stallion ages ranged from 5 to 26 years. Control stallions were bred to 127 and 100 mares and the treatment stallions to 211 and 155 mares in the 2000 and 2001 seasons, respectively. The control and treatment stallions settled mares in 65/215 (30%) and 83/351 (24%) cycles in 2000 and in 53/179 (30%) and 86/223 (39%) cycles in 2001 during the T2-T5 periods, respectively.

Figure 2:
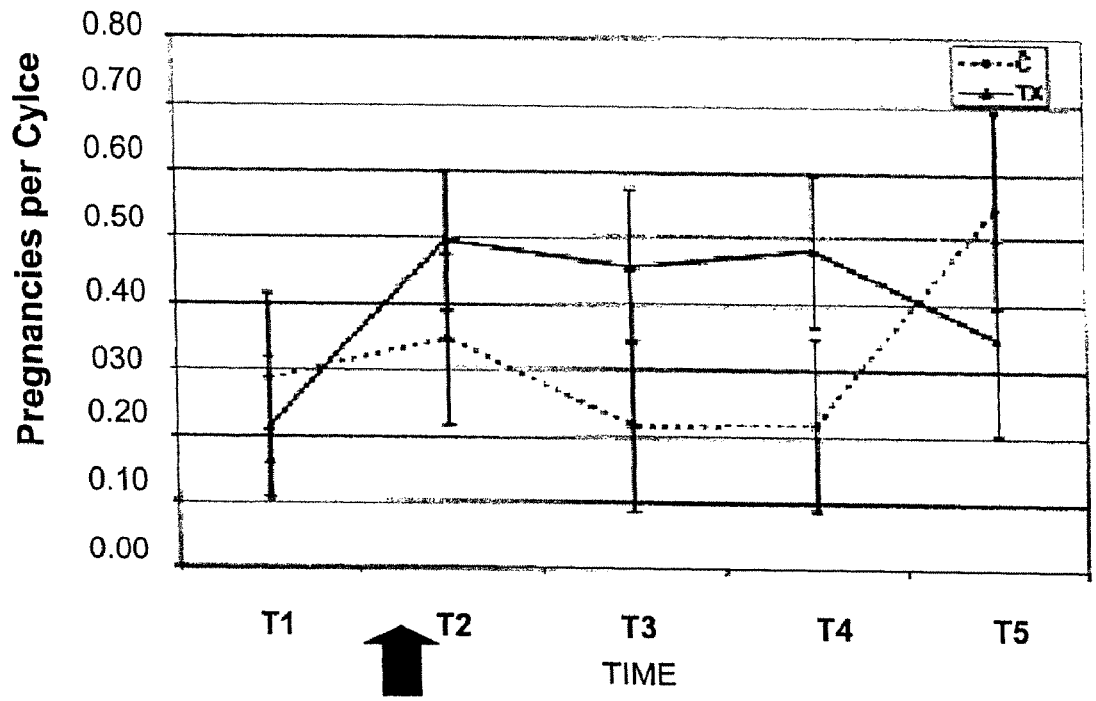
FIG. 2 is a graph of pregnancies per cycle over time demonstrating pregnancies per cycle for treated and control stallions.

The proportion of pregnancies was not different between the 2000 and 2001 season in the T2-T4 periods for the control stallions (P>0.05). Treatment stallions achieved a significantly higher proportion of pregnancies during the same periods T2-T4 in 2001 when compared with the same period in 2000 when they were not receiving the supplement (P<0.05). FIG. 1 and FIG. 2 The increase in proportion of pregnancies was consistent across all the treatment stallions (n=6) while all control stallions (for which 2000 fertility data was available, n=3) experienced a slight decline in fertility during 2001. The proportion of pregnancies did not differ statistically between treatment and control stallions during T2-T4 in 2001 (P>0.05). The LS means for pregnancies per cycle over all time periods in the 2000 and 2001 seasons are presented in FIG. 1 which shows a graph of pregnancies per cycle over time representing that the LS means +/−SE for pregnancies per cycle for stallions assigned to the treatment group (not supplemented in 2000)(n=6), as well as FIG. 2 which shows a graph of pregnancies per cycle over time demonstrating LS means +/−SE for pregnancies per cycle for treated (n=6) and control (n=4) stallions in the 2001 season. The arrow in FIG. 2 indicates time that treatment and placebo were started.

Figure 3:
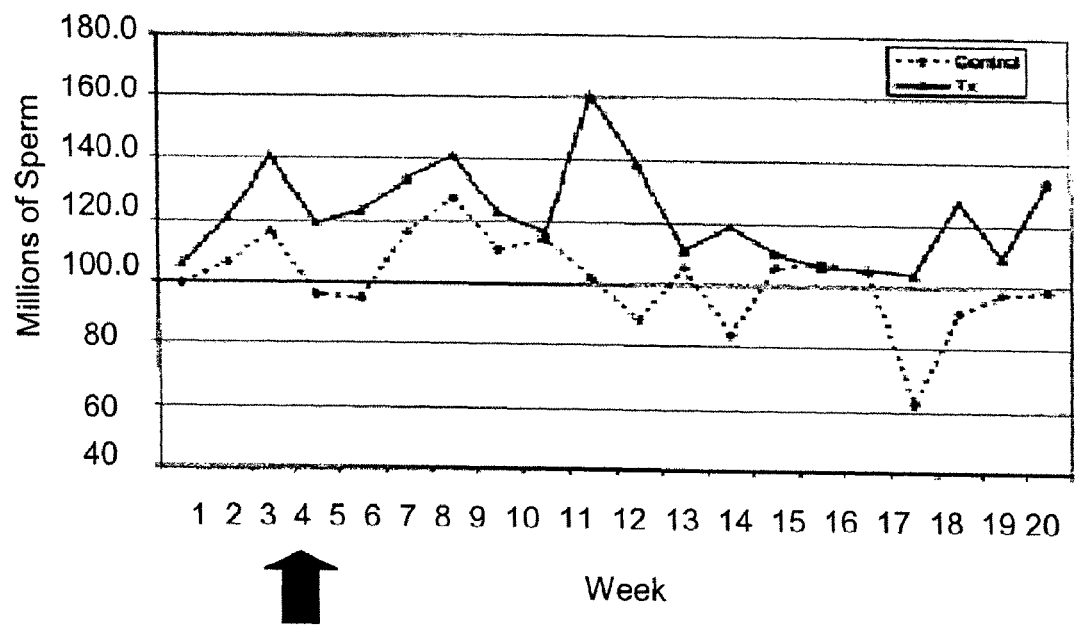
FIG. 3 is a graph of sperm quantity over time demonstrating mean concentration of sperm for treated and control stallions.
Figure 4:
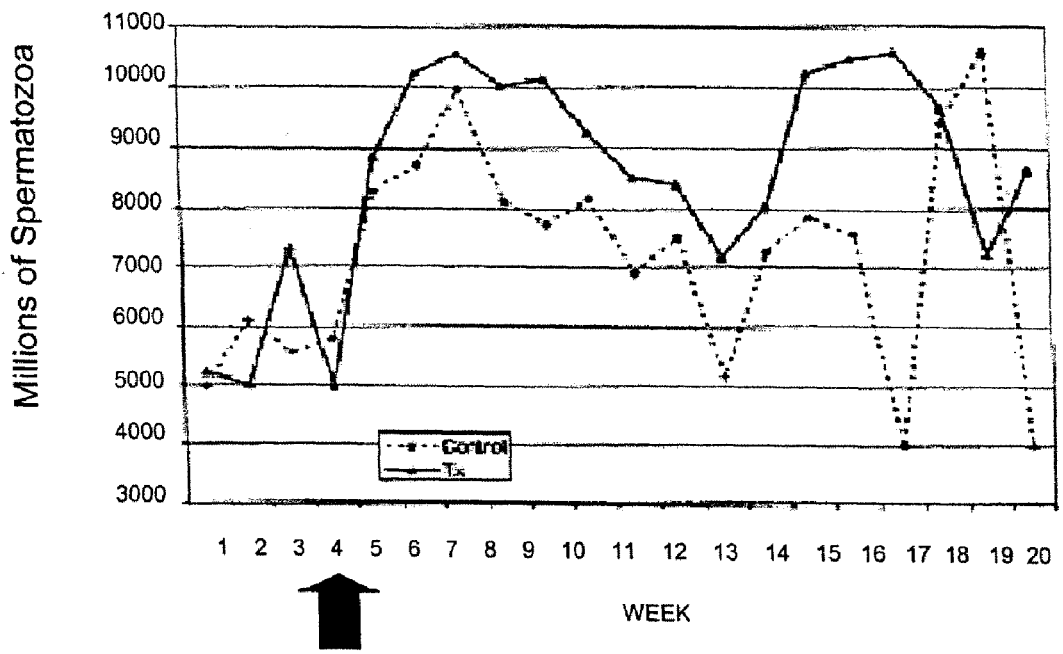
FIG. 4 is a graph of spermatozoa quantity over time demonstrating mean motility for treated and control stallions.
Figure 5:
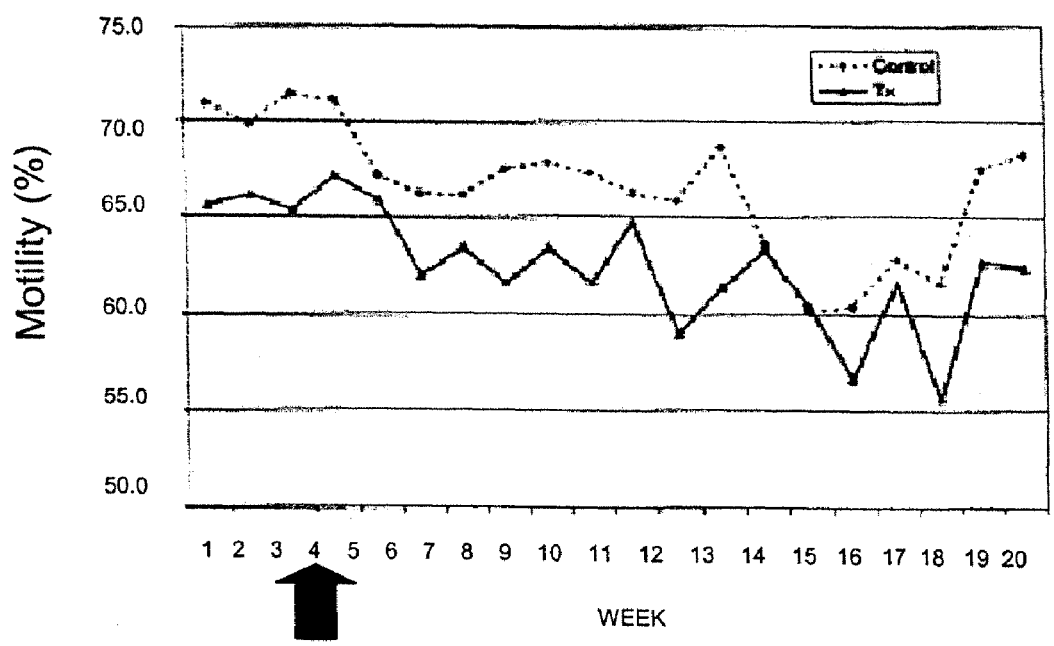
FIG. 5 is a graph showing motility % over time demonstrating motility for treated and control stallions.

Semen was available from all treatment (n=6) and control (n=4) stallions for WK1-15 of the evaluation period in 2001. However, between WK16 and WK20 motility, concentration and total number of sperm data were unavailable in some weeks for some of the stallions. Therefore the results reported for WK16-20 are based on fewer stallions in each group. Mean motility, concentration and total number of sperm were not significantly different (P=0.888, 0.958, and 0.567, respectively) between the treatment and control stallions during the 20-week evaluation period in the 2001 season. This is accurately demonstrated by making references to FIG. 3, FIG. 4, and FIG. 5. FIG. 3 shows a graph of sperm quantity over time (weeks) demonstrating mean concentration of sperm for treated (n=6) and control (n=4) stallions in the 2001 season. An arrow in FIG. 3 indicates time that treatment and placebo were started. Weeks 16 through 20 data points represent fewer than all stallions. FIG. 4 shows a graph of spermatozoa quantity over time demonstrating mean motility for treated (n=6) and control (n=4) stallions in the 2001 season. The arrow in FIG. 4 indicates time that treatment and placebo were started. Weeks 16 through 20 data points represent fewer than all stallions. FIG. 5 shows a graph of motility (%) over time (weeks) demonstrating mean motility for treated (n=6) and control (n=4) stallions in the 2001 season. An arrow indicates time that treatment and placebo were started. Weeks 16-20 data points represent fewer than all stallions.

Figure 6:
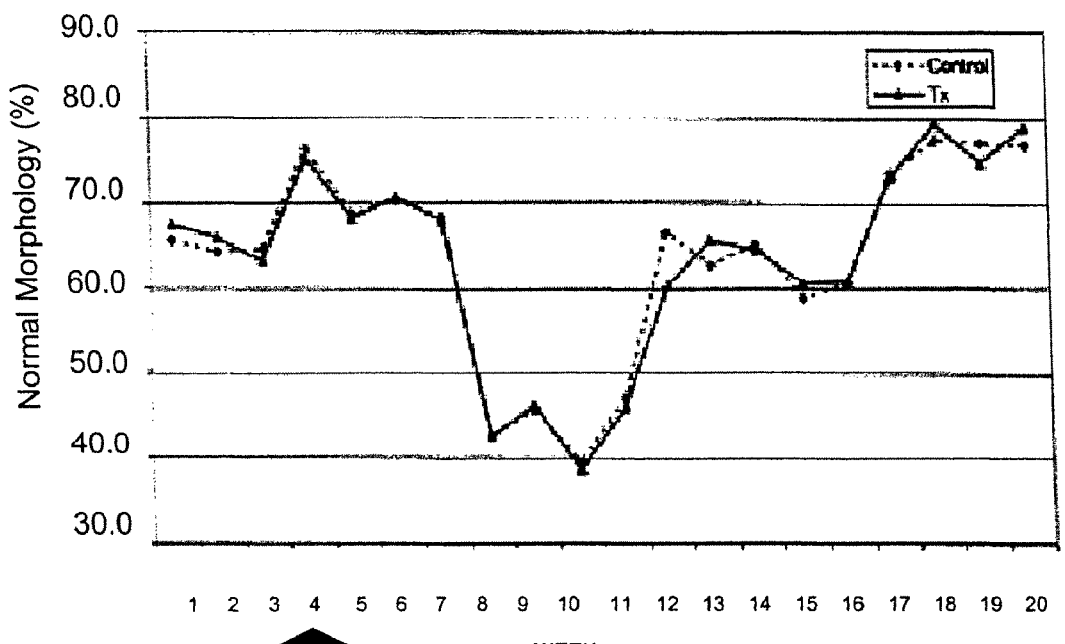
FIG. 6 is a graph showing normal morphology % over time demonstrating mean normal sperm morphology for treated and control stallions.
Figure 7:
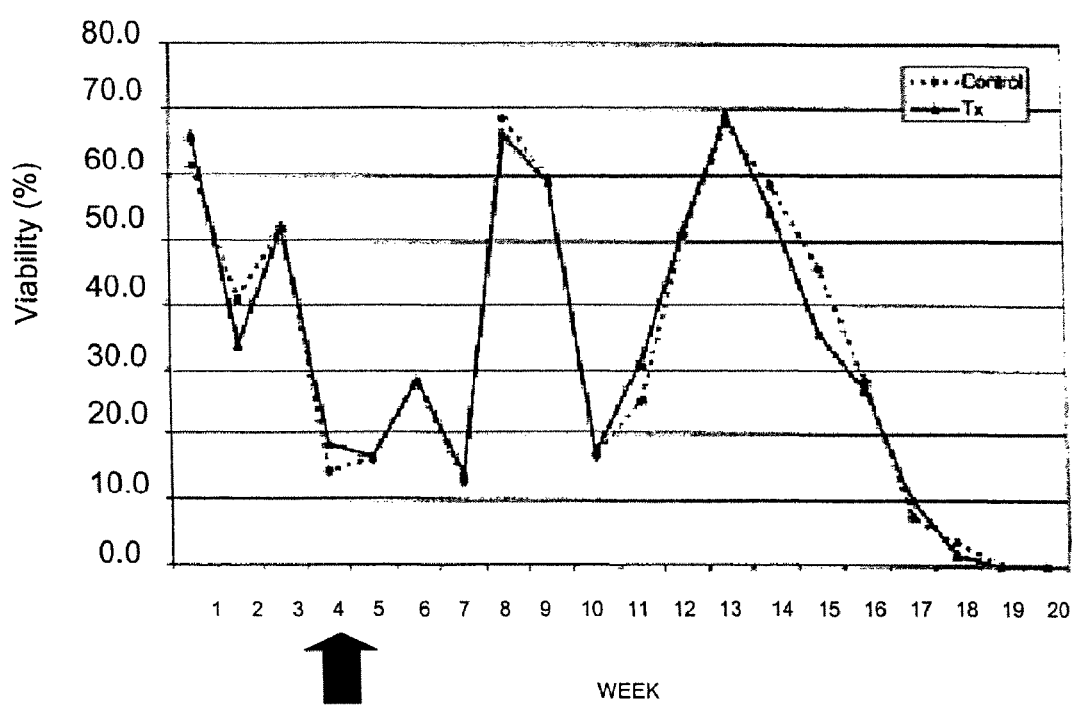
FIG. 7 is a graph showing viability (%) over time demonstrating mean viability for treated and control stallions.

Morphology and viability data was available for all stallions during the entire 20-week semen evaluation period. Mean normal morphology and sperm viability varied considerably during the evaluation period. However neither were different (P=0.929 and 0.774, respectively) between the treatment and control stallions. This is accurately demonstrated by making reference to FIG. 6 and FIG. 7. FIG. 6 is a graph showing normal morphology % over time demonstrating mean normal sperm morphology for treated (n=6) and control (n=4) stallions in the 2001 season. An arrow indicates time that treatment and placebo were started. Weeks 16 through 20 data points represent fewer than all stallions. FIG. 7 is a graph showing viability (%) over time demonstrating mean viability for treated (n=6) and control (n=4) stallions in the 2001 season. An arrow in FIG. 7 indicates time that treatment and placebo were started.

Apparently many nutrients appear to play in role in the development and function of sperm. Detailed knowledge of the role played by various nutrients or the level required for optimal development and function of sperm is not well understood. This example evaluated the effect of a nutritional supplement designed to provide a combination of ingredients to benefit the reproductively active stallion. Fertility was improved among stallions receiving the nutritional supplement over that observed during the previous breeding season. Loss of 2 control group stallions may have contributed to an inability to demonstrate a statistically significant difference in proportion of pregnancies among treatment and control groups for the 2001 season. The proportion of pregnancies increased significantly during the treatment period, T2-T4 in 2001 compared with the same time period in 2000 while fertility among control stallions remained unchanged. This study ruled out morphological and number of sperm as the mechanism for the increased conception rate. This leaves enhanced attachment site structures as leading mode of action.

This case demonstrates the efficacy of the compositions of the present invention. The pregnancies of the animals after treatment demonstrate the improvement in the conditions of the disorder from which the animal suffered prior to treatment with one composition of the present invention.

Obviously, many modifications may be made without departing from the basic spirit of the present invention. Accordingly, it will be appreciated by those skilled in the art that within the scope of the appended claims, the invention may be practiced other than has been specifically described herein.

What is claimed is:

1. A method for improving fertility in a mammal in need of a conception, implantation, or gestation promoting treatment comprising administering to a mammal in need thereof a, conception, implantation, or gestation promoting effective amount of a nutraceutical composition comprising a glucosamine component in an effective proportion,
   wherein said glucosamine component is a chemical selected from the group consisting of glucosamine sulphate, glucosamine sulfate potassium chloride (glucosamine sulfate 2KCl, glucosamine sulfate sodium chloride (glucosamine sulfate NaCl, glucosamine hydrochloride, N-acetylglucosamine, Poly N-acetylglucosamine, and combinations thereof.

2. The method of claim 1, wherein the nutraceutical composition is in an oral liquid dosage form, or a powder form.

3. The method of claim 1, wherein the conception, implantation, or gestation promoting effective amount is a gametogenesis promoting effective amount.

4. The method of claim 3, wherein the nutraceutical composition comprises the following constituents:
   a) an oil cake component,
   b) the glucosamine component,
   c) an acid component,
   d) a mineral component,
   e) a vitamin component; and
   f) a functional food component, wherein each of the constituents is present in the composition in an effective proportion.

5. The method of claim 4, wherein said effective proportion further comprises:
   a) between about 50 and about 200 parts by weight (pbw) oil cake component,
   b) between about 400 to 750 pbw glucosamine component,
   c) between about 50 and about 150 pbw acid component,
   d) between about 0.0001 and about 1 pbw mineral component,
   e) between about 0.0001 and about 1 pbw vitamin component, and
   f) between about 0.0001 and about 1 pbw of functional food component.

6. The method of claim 5, wherein said acid component is ascorbic acid and at least one derivative thereof, lipoic acid, or dihydrolipoic acid, wherein the derivative is selected from the group consisting of magnesium ascorbyl phosphate, sodium ascorbyl phosphate, sodium ascorbate, ascorbyl glucoside, and combinations thereof.

7. The method of claim 6, wherein said mineral component further comprises at least one mineral selected from the group consisting of zinc, boron, chromium, manganese, and combinations thereof.

8. The method of claim 7, wherein said nutraceutical composition comprises an amino acid chelate.

9. The method of claim 8, wherein said vitamin component further comprises at least one vitamin selected from the group consisting of biotin, thiamine hydrochloride, folic acid, and combinations thereof.

10. The method of claim 9, wherein said functional food component further comprises at least one ingredient selected from the group consisting of prebiotic, probiotic, synbiotic, and combinations thereof.

11. The method of claim 10, wherein the oil cake component is selected from the group consisting of vegetable oil cake, soybean flower, linseed oil cake, cottonseed oil cake, peanut oil cake, safflower oil cake, coconut oil cake, palm oil cake, sesame oil cake, sunflower oil cake, rapeseed oil cake, kapok oil cake, mustard seed oil cake, and combinations thereof.

12. The method of claim 1, wherein said glucosamine component is a chemical selected from the group consisting of glucosamine sulphate, glucosamine sulfate 2KCl, glucosamine sulfate NaCl, and combinations thereof.

13. The method of claim 1, wherein said glucosamine component is a chemical selected from the group consisting of glucosamine sulphate, glucosamine sulfate 2KCl, and combinations thereof.

14. The method of claim 1, wherein said glucosamine component is glucosamine sulfate 2KCl.

15. The method of claim 1, further comprising identifying the mammal as needing a conception, implantation, or gestation promoting treatment.

16. The method of claim 1, wherein the mammal is a male.

17. The method of claim 1, wherein the mammal is a female.

* * * * *